United States Patent
Rosenblum et al.

(10) Patent No.: US 8,968,243 B2
(45) Date of Patent: Mar. 3, 2015

(54) DEVICE AND METHOD FOR DELIVERING MEDICINE INTO THE TYMPANIC CAVITY, WITH SLIDING ASSIST

(75) Inventors: Lev Rosenblum, Salt Lake City, UT (US); Christian Pfeffer, Sommerville, MA (US); George Kenney, Medfield, MA (US)

(73) Assignee: EntraTympanic, LLC, Medfield, MA (US)

( * ) Notice: Subject to any disclaimer, the term of this patent is extended or adjusted under 35 U.S.C. 154(b) by 339 days.

(21) Appl. No.: 13/635,035

(22) PCT Filed: Mar. 14, 2011

(86) PCT No.: PCT/US2011/028414
§ 371 (c)(1),
(2), (4) Date: Sep. 14, 2012

(87) PCT Pub. No.: WO2011/115936
PCT Pub. Date: Sep. 22, 2011

(65) Prior Publication Data
US 2013/0023818 A1    Jan. 24, 2013

Related U.S. Application Data

(60) Provisional application No. 61/314,018, filed on Mar. 15, 2010.

(51) Int. Cl.
*A61M 37/00* (2006.01)
*A61F 11/00* (2006.01)
*A61M 31/00* (2006.01)

(52) U.S. Cl.
CPC .............. *A61F 11/002* (2013.01); *A61M 31/00* (2013.01)
USPC .......................................... 604/141

(58) Field of Classification Search
CPC ............ A61M 1/0058; A61M 1/0084; A61M 1/0064; A61M 3/0233; A61M 2210/00; A61M 2210/0662; A61M 2210/0668; A61M 2210/0675
USPC .............. 604/28, 141, 35, 506, 140, 147, 187
See application file for complete search history.

(56) References Cited

U.S. PATENT DOCUMENTS 3,768,472 A  * 10/1973 Hodosh et al. ................. 604/143
3,888,258 A    6/1975 Akiyama
(Continued)

FOREIGN PATENT DOCUMENTS

EP          0271775        12/1987
WO         97-02784         1/1997
(Continued)

OTHER PUBLICATIONS

PCT Written Opinion for PCT/US2010/052569 dated Jun. 12, 2010.
(Continued)

*Primary Examiner* — Hung Q Nguyen
*Assistant Examiner* — Nilay Shah
(74) *Attorney, Agent, or Firm* — Wolf, Greenfield & Sacks, P.C.

(57) ABSTRACT

A device for substance delivery to and/or extraction from the tympanic cavity, comprising: a stationary body having a distal surface, a proximal surface; a movable body having a distal surface and a proximal surface, disposed within the stationary body and free to move relative to the stationary body; at least one piercing element having a distal end and a proximal end, disposed in the movable body; and a means for moving the movable body relative to the stationary body.

20 Claims, 7 Drawing Sheets

SECTION A-A

(56) References Cited

U.S. PATENT DOCUMENTS

| | | | |
|---|---|---|---|
| 4,468,218 A | 8/1984 | Armstrong | |
| 4,641,663 A | 2/1987 | Juhn | |
| 4,799,921 A * | 1/1989 | Johnson et al. | 604/506 |
| 4,838,877 A | 6/1989 | Massau | |
| 5,309,899 A * | 5/1994 | Ginsberg | 604/38 |
| 5,709,677 A | 1/1998 | Slatkine | |
| 5,741,250 A | 4/1998 | Garito | |
| 5,997,500 A * | 12/1999 | Cook et al. | 604/60 |
| 6,024,726 A | 2/2000 | Hill | |
| 6,258,067 B1 | 7/2001 | Hill | |
| 6,293,940 B1 | 9/2001 | Slatkine | |
| 6,390,975 B1 | 5/2002 | Walls | |
| 6,416,512 B1 | 7/2002 | Ellman | |
| 6,475,138 B1 | 11/2002 | Schechter | |
| 6,522,827 B1 | 2/2003 | Loeb | |
| 6,770,080 B2 | 8/2004 | Kaplan | |
| 7,351,246 B2 | 4/2008 | Epley | |
| 2002/0010428 A1 | 1/2002 | Vedrine | |
| 2002/0049414 A1* | 4/2002 | Nobles et al. | 604/187 |
| 2002/0161379 A1 | 10/2002 | Kaplan | |
| 2004/0106553 A1 | 6/2004 | Alekshun | |
| 2004/0133099 A1 | 7/2004 | Dyer | |
| 2005/0019256 A1 | 1/2005 | Dobkine | |
| 2005/0137575 A1* | 6/2005 | Thompson et al. | 604/522 |
| 2005/0182385 A1 | 8/2005 | Epley | |
| 2005/0256499 A1 | 11/2005 | Pettis | |
| 2005/0271711 A1 | 12/2005 | Lynch | |
| 2006/0106343 A1 | 5/2006 | Alchas | |
| 2006/0155304 A1 | 7/2006 | Kaplan | |
| 2006/0195165 A1 | 8/2006 | Gertner | |
| 2006/0253087 A1 | 11/2006 | Vlodaver | |
| 2007/0167918 A1* | 7/2007 | Reed et al. | 604/187 |
| 2007/0203454 A1 | 8/2007 | Shermer | |
| 2008/0097414 A1 | 4/2008 | Li | |
| 2008/0132824 A1 | 6/2008 | Epley | |
| 2008/0208297 A1 | 8/2008 | Gertner | |
| 2008/0262510 A1 | 10/2008 | Clifford | |
| 2008/0294255 A1 | 11/2008 | Gonzales | |
| 2009/0149922 A1 | 6/2009 | White | |
| 2009/0149924 A1 | 6/2009 | White | |
| 2009/0185191 A1 | 7/2009 | Boppart | |
| 2011/0015645 A1 | 1/2011 | Liu et al. | |

FOREIGN PATENT DOCUMENTS

| | | |
|---|---|---|
| WO | 99-55218 | 11/1999 |
| WO | 00-10627 | 3/2000 |
| WO | 02-083230 | 10/2002 |
| WO | 2005-115527 | 12/2005 |
| WO | 2006-078924 | 7/2006 |
| WO | 2006-119512 | 11/2006 |
| WO | 2007-140079 | 12/2007 |
| WO | WO2011008948 | 1/2011 |

OTHER PUBLICATIONS

PCT International Search Report and the Written Opinion dated May 3, 2011 for PCT/US2011/028414 Mar. 5, 2011.

* cited by examiner

List of elements

| Position # | Name |
|---|---|
| 1 | Movable body |
| 1a | Large section of the movable body |
| 1b | Small section of the movable body |
| 1c | Distal surface of the movable body |
| 1d | Proximal surface of the movable body |
| 2 | Stationary Body |
| 2a | Large section of the stationary body |
| 2b | Small section of the stationary body |
| 2c | Distal surface of the stationary body |
| 2d | Proximal surface of the stationary body |
| 3 | Housing insert |
| 4 | Printed circuit board (PCB) |
| 5 | Housing |
| 6 | Handle |
| 7 | X-axis |
| 8 | Y-axis |
| 9 | Z-axis |
| 10a | Piercing element connected to injection chamber |
| 10b | Piercing element connected to evacuation chamber |
| 11a | Injection chamber |
| 11b | Evacuation chamber |
| 12a | Injection chamber plunger |
| 12b | Evacuation chamber plunger |
| 13 | Magnetizable insert |
| 14 | Front lens |
| 15 | Vent channel |
| 18 | Viewing opening |
| 20 | Outer compressible layer of the stationary body |
| 20a | Inner rigid layer of the stationary body |
| 21 | Lock-in notch |
| 22 | Back seal |
| 23a | 10a piercing element contact |
| 23b | 10b piercing element contact |
| 24a | First stationary body contact |
| 24b | Second stationary body contact |
| 25 | Stationary body vacuum connect |
| 26 | Vacuum channels |
| 26a | Vacuum ports (7 places) |
| 27 | Front guide |
| 30 | Vacuum fitting |
| 31 | Electromagnetic clamp (2 places) |
| 31a | Compression layer of electromagnetic clamp |
| 32a | First insert contact |
| 32b | Second insert contact |
| 33 | Stopper ball |
| 34 | Stopper spring |
| 40 | LED |
| 41 | Electromagnet |
| 42 | Ohmmeter module |
| 43 | CPU |
| 44 | Speaker |
| 45 | Selector panel |
| 46 | Power button |
| 47 | Select button for filled-chamber cartridge |
| 48 | Select button for empty cartridge |
| 50 | Magnifying lens |
| 60 | Vacuum button-valve combination |
| 61 | Vacuum line |
| 62 | Main power supply line |
| 99 | Flat head screw (16 places) |

FIGURE 1

SECTION A-A

SECTION B-B

DEVICE AND METHOD FOR DELIVERING MEDICINE INTO THE TYMPANIC CAVITY, WITH SLIDING ASSIST

CROSS REFERENCE OF RELATED APPLICATIONS

This application is a national is a national stage filing under 35 U.S.C. §371 of international PCT application PCT/US2011/028414, filed Mar. 14, 2011, which claims priority to U.S. Provisional Application No. 61/314,018, filed Mar. 15, 2010, the entire contents of each of which is incorporated herein by reference.

FIELD OF INVENTION

This invention relates, generally, to otologic devices and methods of treatments of various ear-related disorders, and more specifically to delivering medicine into the tympanic cavity.

BACKGROUND OF THE INVENTION

The device and method in the present invention relate to delivery of medicine to the middle and/or inner ear and evacuation of fluid, if any, located in the tympanic cavity. The device and the method can be used, for example, for treatment and/or prevention of various ear-related ailments, such as acute otitis media.

It is frequently desirable to deliver various types of medicine into the tympanic cavity. Such medicine can be directed at treating ailments of the middle as well as the inner ear. For example, medically effective amounts of antibiotic and/or anti-inflammatory drug(s) can be delivered through the tympanic membrane to treat middle ear infections. Currently, delivery of the drugs into the tympanic cavity is usually done when the tympanic membrane has ruptured or the patient has a previously-inserted tube in the membrane, that is, non-surgical delivery of medicine to the tympanic cavity is usually done only when there is an existing perforation in the tympanic membrane, through which the medicine is delivered. The majority of the patients, however, do not have an existing perforation through which medicine can be delivered; consequently, such procedure is not available to them.

Alternatively, a physician can use a syringe to inject medicine through the tympanic membrane. However, this procedure can be dangerous for several reasons. First, the tympanic cavity houses a variety of vulnerable structures, such as the malleus, incus, stapes, facial nerve, and in some cases carotid artery. An accidental contact with any of these structures can result in adverse effects that range from pain and severe bleeding (in case of a punctured carotid artery or branches of the internal jugular vein) to permanent disability, such as hearing loss.

Any incisions and/or perforations of the tympanic membrane in the posterosuperior and anterosuperior quadrants are highly discouraged because the most vulnerable structures located in the tympanic cavity are positioned proximately behind these two quadrants. Consequently, incisions and/or perforations of the tympanic membrane are usually performed in the posteroinferior and anteroinferior quadrants. Further, incisions and/or perforations made in the posteroinferior and anteroinferior quadrants must also be done with extreme care, and accidental penetration more than a minimal depth beyond the normal physiological position of the tympanic membrane can cause severe injuries. Because the physician must insert the needle in a tiny area and with minimal penetration, the margin for error is very small. Consequently, incisions and/or penetrations of the tympanic membrane in children are usually performed under general anesthesia, to avoid accidental over-penetration or an unwanted penetration in a wrong location (for example, a perforation in the posterosuperior quadrant or contact with the ear canal) as a result of the child's inability to remain stationary during the procedure.

This invention offers a novel way of safely delivering desired amounts of medicine into, as well as aspirating fluid from, the tympanic cavity. The invention allows evacuation of fluid from the tympanic cavity, delivery of medicine into the tympanic cavity, and/or biopsy of the tympanic membrane by making a minute perforation in the membrane. Furthermore, the invention allows the procedure to be performed quickly, safely and without general anesthesia by limiting the depth and location of the penetration on the tympanic membrane. The invention also allows for safe removal of fluid accumulated in the tympanic cavity and subsequent analysis of the fluid. Such analysis, for example, may include a test for the presence of bacteria and a determination of the type of bacteria present. Consequently, the invention will reduce the need for systemic treatment of ailments related to middle and inner ear in patients who do not have a perforated tympanic membrane, especially in children.

One of the major deficiencies of the current devices is the potential to make contact with crucial physiological structures behind the membrane, injuring the patient. This potential for injury is amplified in young patients. Although an adult patient is likely to comply with a request to remain stationary while the physician injects him with a four-inch needle, a child is likely to ignore such request.

SUMMARY OF THE INVENTION

This invention is directed at delivering medicine to the middle and inner ear as well as evacuating fluid, if any, located in the tympanic cavity. This device overcomes the deficiencies of prior devices by eliminating the potential for penetrating into the tympanic cavity beyond the normal physiological position of the tympanic membrane. By doing so, this device presents a novel and safe way for delivering medicine into and/or removing fluid from the tympanic cavity. Instead of penetrating the tympanic membrane by plunging a needle through the membrane and into the tympanic cavity, the present invention allows to flex the membrane toward a movable body and keep the movable body in contact with the tympanic membrane after at least one piercing element punctures the membrane. Because no piercing element enters the tympanic cavity beyond the normal physiological position of the tympanic membrane, there is no risk of contact with any of the structures in the tympanic cavity. The invention also facilitates one or more fluid-holding chambers in the movable body of the device, which may hold substance that would be injected into and/or fluid that would be evacuated from the tympanic cavity. Multiple piercing elements can be used. For example, one hollow piercing element can be used to inject the medicine into the tympanic cavity and another to evacuate the fluid from the tympanic cavity. Alternatively, a double-walled piercing element (for example, a double-lumen needle) can also be used. Additionally, a hollow piercing element can be used to obtain a biopsy of the tympanic membrane tissue, which can be later analyzed. After the evacuation of fluid, the injection of medicine, and/or the biopsy are completed, the tympanic membrane is released and will return to its normal physiological position. Subsequently, the device is removed from the patient's ear canal.

BRIEF DESCRIPTION OF THE DRAWINGS

FIG. 1 shows the list of elements.

DETAILED DESCRIPTION OF THE PREFERRED EMBODIMENTS

Below is the description of the preferred embodiments of this invention. It is recognized, however, that other embodiments would be obvious to those skilled in the art.

Figure 2:
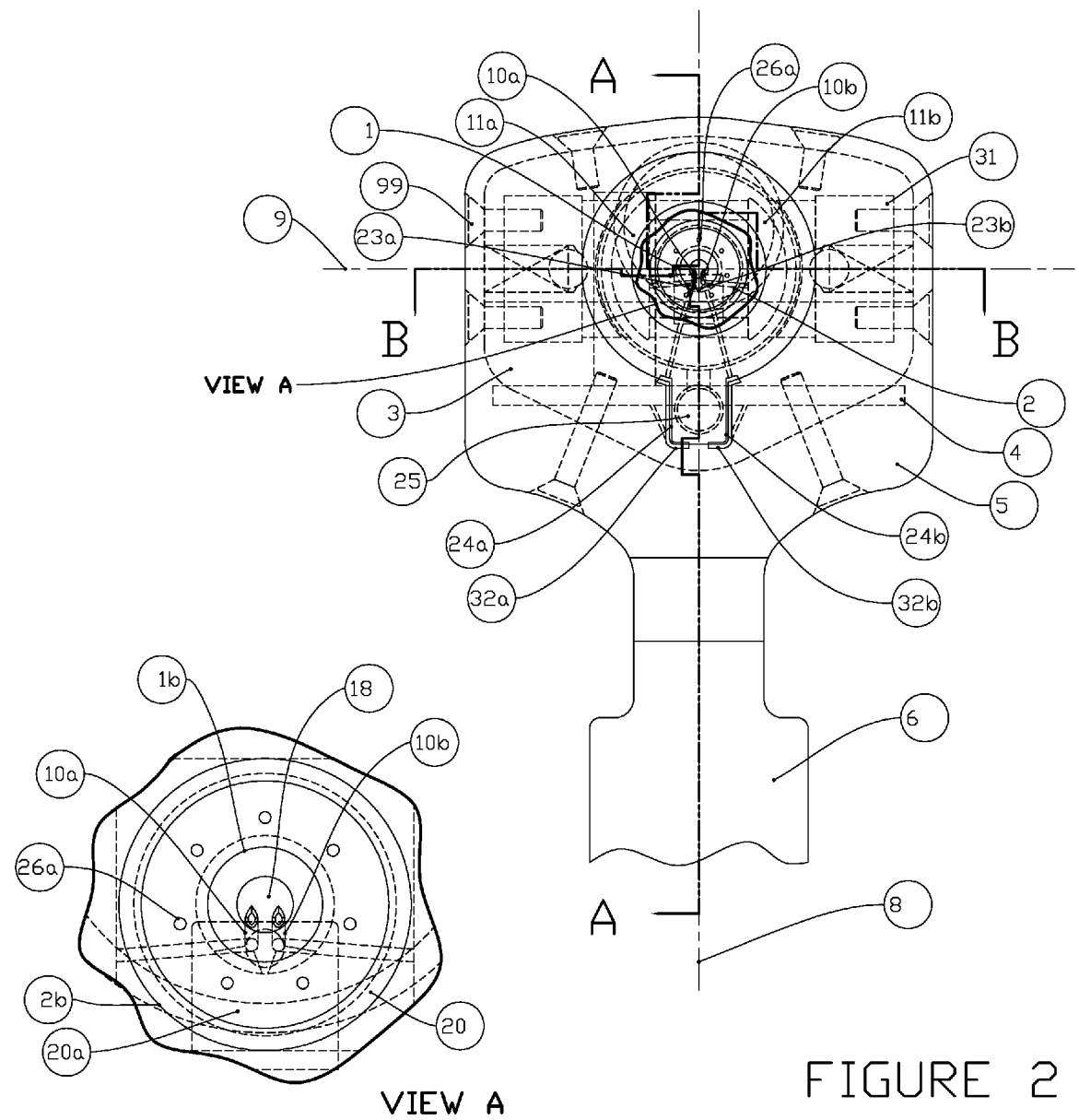
FIG. 2 shows the front view of the device.
Figure 3:
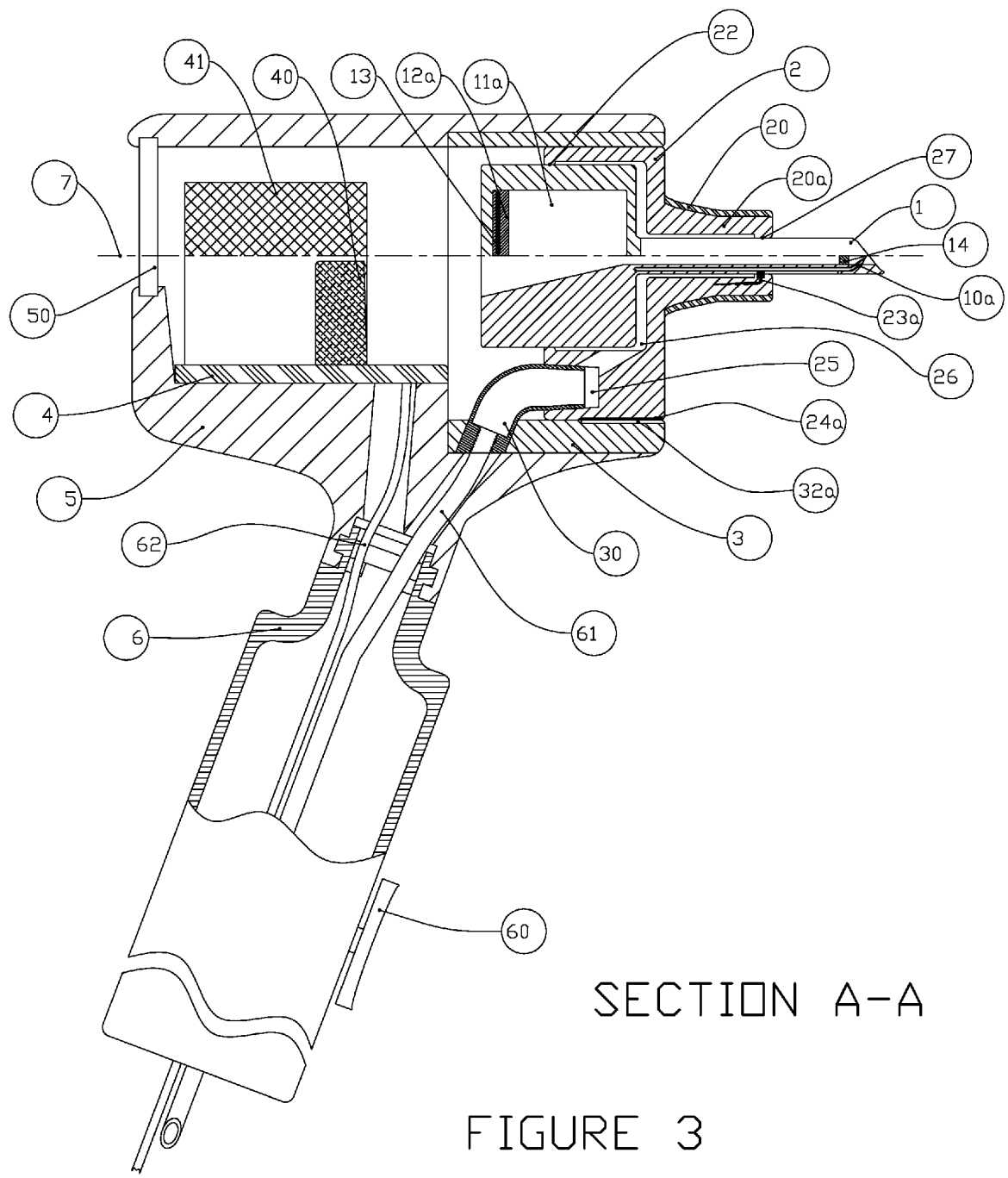
FIG. 3 shows the Section A-A of the device in a fully-extended position.
Figure 4:
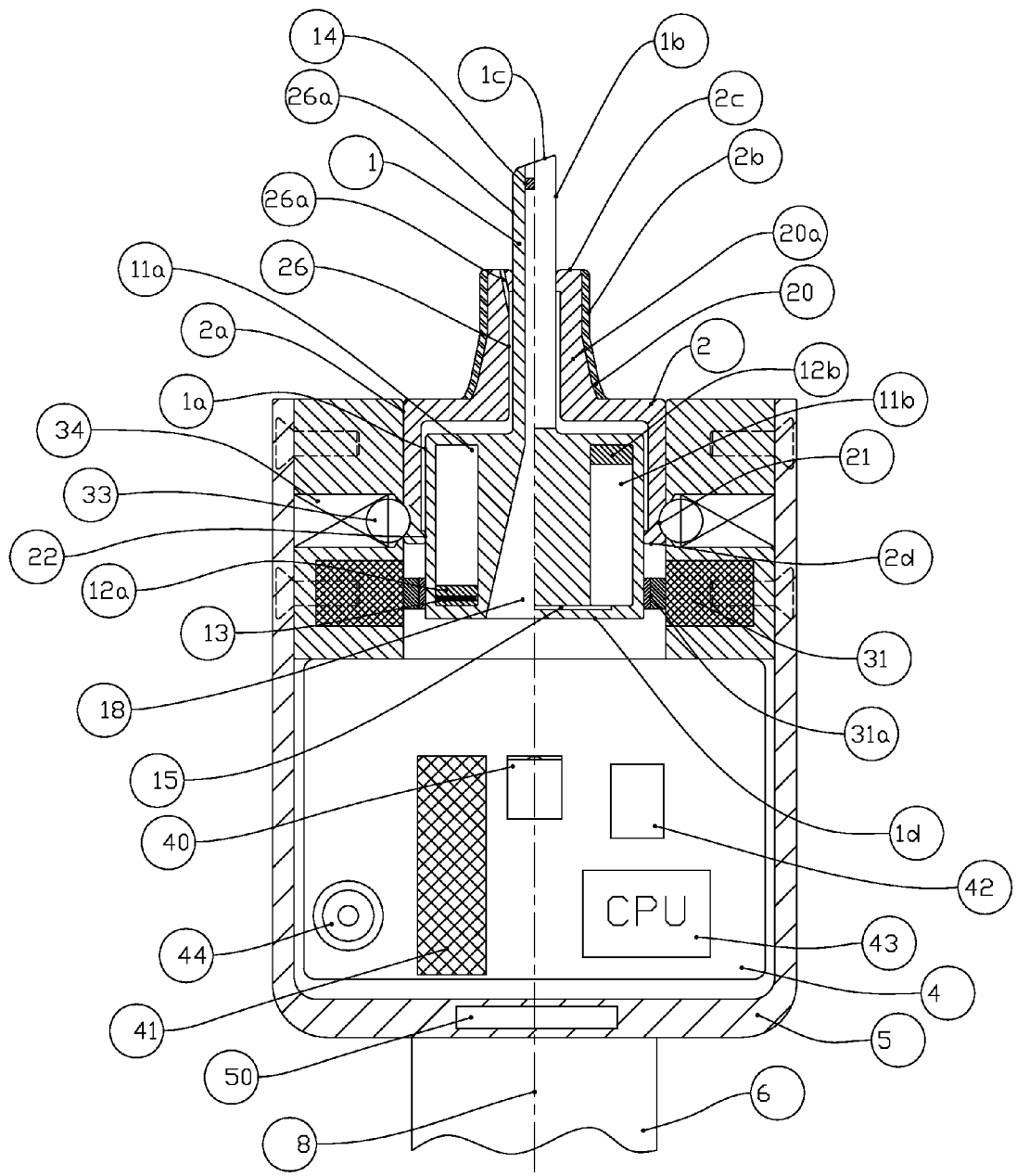
FIG. 4 shows the Section B-B of the device in a fully-extended position.

The front view of the device assembly is-shown in FIG. 2 shows the locations of section views A-A and B-B, displayed in FIGS. 3 and 4, respectively. In the preferred embodiment, the device is comprised of the following elements, shown in FIGS. 2, 3, and 4: movable body 1, stationary body 2, housing insert 3, printed circuit board 4, housing 5, and handle 6. In the preferred embodiment, an insert 3 is used mainly for ease of assembly of the device; it is affixed in the housing 5 with flat head screws 99. The housing 5 and handle 6 are made from 6061-T6 aluminum, and the housing insert 3 is made from Teflon® PTFE Grade 860 (polytetrafluoroethylene). However, many other materials are suitable for the housing 5, handle 6, housing insert 3 as well as other components of the device, which are known or would be obvious to those skilled in the art. Further, other configurations, which would not change the basic functionality of the device, for example a device without the handle 6, would be obvious to those skilled in the art.

The movable body 1 is disposed within the stationary body 2, and the pair is inserted into the housing insert 3, as shown in FIGS. 2, 3, and 4. The stationary body is held in place using a stopper ball 33 and stopper spring 34 combinations, as shown in FIG. 4. There are many other methods of securing the movable body 1 and stationary body 2 pair in the device, which are known to those skilled in the art. In the preferred embodiment, the movable body 1 and stationary body 2 are designed to be disposable and are removable from the housing 5. However, other configurations of the device—for example, where the housing 5 and the stationary body 2 would be a single element—are known or would be obvious to those skilled in the art.

As shown in FIGS. 2, 3, and 4, in the preferred embodiment, the movable body 1 comprises: the large section of the movable body 1a, the small section of the movable body 1b, the distal surface of the movable body 1c, and the proximal surface of the movable body 1d. The large section of the movable body 1a and the small section of the movable body 1b are essentially cylindrical. However, other suitable shapes can be used and would be obvious to those skilled in the art. Further, an injection chamber 11a; evacuation chamber 11b; piercing element 10a connected to the injection chamber 11a; and piercing element 10b connected to the evacuation chamber 11b are disposed in the movable body 1.

As shown in FIGS. 2, 3 and 4, in the preferred embodiment, the distal surface of the movable body 1c is disposed approximately in a plane oriented at a compound angle with respect to the x-axis 7, such that when the device is inserted into the ear, the distal surface of the movable body 1c can be aligned to be approximately parallel to the tympanic membrane. That is, the distal surface of the movable body 1c is disposed approximately in a plane that is at an angle with respect to the plane formed by the x-axis 7 and y-axis 8, and at an angle with respect to the plane formed by x-axis 7 and z-axis 9, as shown in FIGS. 2, 3, and 4. It is recognized that the distal surface of the movable body 1c can be disposed at various angles with respect to planes formed by x-axis 7 and y-axis 8, x-axis 7 and z-axis 9, and y-axis 8 and z-axis 9. For example, the distal surface of the movable body 1c can be approximately disposed in a plane normal to the x-axis 7, which would be parallel to a plane formed by the y-axis 8 and z-axis 9. Furthermore, the distal surface of the movable body 1c can have various shapes; for example, it can approximate the shape of the tympanic membrane.

One or more piercing elements can be disposed in the movable body; and some or all of the piercing elements can be either solid or hollow. Further, some or all of the piercing elements can be connected to a chamber capable of holding substance or can be standalone (unconnected). In the preferred embodiment, two hollow piercing elements 10a and 10b, which are connected to two chambers 11a and 11b, respectively, are used, as shown in FIGS. 2 and 4. Because the hollow piercing element(s) are capable of holding fluid inside the hollow portion of the shaft, the element(s) can also serve as fluid-holding chamber(s). After the tympanic membrane is punctured, a substance (if any) located in the injection chamber 11a can be delivered through the piercing element 10a into the tympanic cavity. Simultaneously, any fluid located in the tympanic cavity can be evacuated through the piercing element 10b, into the evacuation chamber 11b, as shown in FIGS. 2, 3 and 4, which is connected to the evacuation chamber 11b. A biopsy of the tympanic membrane can also be obtained from the evacuation chamber or a piercing element designed for biopsy can be used.

In the preferred embodiment, the movable body 1 is made from medical grade polypropylene, and the piercing elements 10a and 10b are fixed in place with a light curing adhesive, such as DYMAX MD® 1162-M. There are many other materials for and methods of manufacturing the same, which are known to those skilled in the art.

In the preferred embodiment, the viewing opening 18 and front lens 14 are disposed in the movable body, as shown in FIGS. 2, 3, and 4. The user can see the tympanic membrane through the viewing opening 18 before advancing the movable body 1 and piercing the membrane. The viewing opening improves the safety of the device by allowing the user to view the tympanic membrane while the movable body is advanced toward the membrane. Other mechanisms known to those skilled in the art can also be used to view the tympanic membrane. For example, an endoscope or other video visualization devices can be used. In the preferred embodiment, the front lens 14 is disposed in the small section of the movable body 1b part of the viewing opening 18, and in some embodiments it may be unnecessary all together. However, the lens can be disposed anywhere along the viewing opening 18. Further, the lens may be a magnifying lens. There are many suitable materials that the lens 14 can be made from. For example, the lens can be made from a clear plastic such as Lexan®. To illuminate the ear canal and the tympanic membrane, an LED 40 is used, as shown in FIGS. 3 and 4. A magnifying lens 50 is disposed in the housing 5, as shown in FIGS. 3 and 4. The magnifying lens 50 improves visibility of the tympanic membrane during the use of the device.

As shown in FIGS. 2, 3, and 4, in the preferred embodiment, the stationary body 2, comprises: large section of the stationary body 2a, small section of the stationary body 2b, distal surface of the stationary body 2c, and proximal surface of the stationary body 2d. The movable body 1 is disposed within the stationary body 2 and is free to move axially toward the tympanic membrane (inward) and away from the tympanic membrane (outward). In the preferred embodiment, the movable body 1 is induced to move inward when a slight vacuum is created in the ear canal. The pressure difference created by the slight vacuum in the ear canal creates a force on the movable body 1 that equals to the vacuum×area of the cross-section of the large section of the movable body 1a. This force pushes the movable body inward, toward the tympanic membrane.

Figure 6:
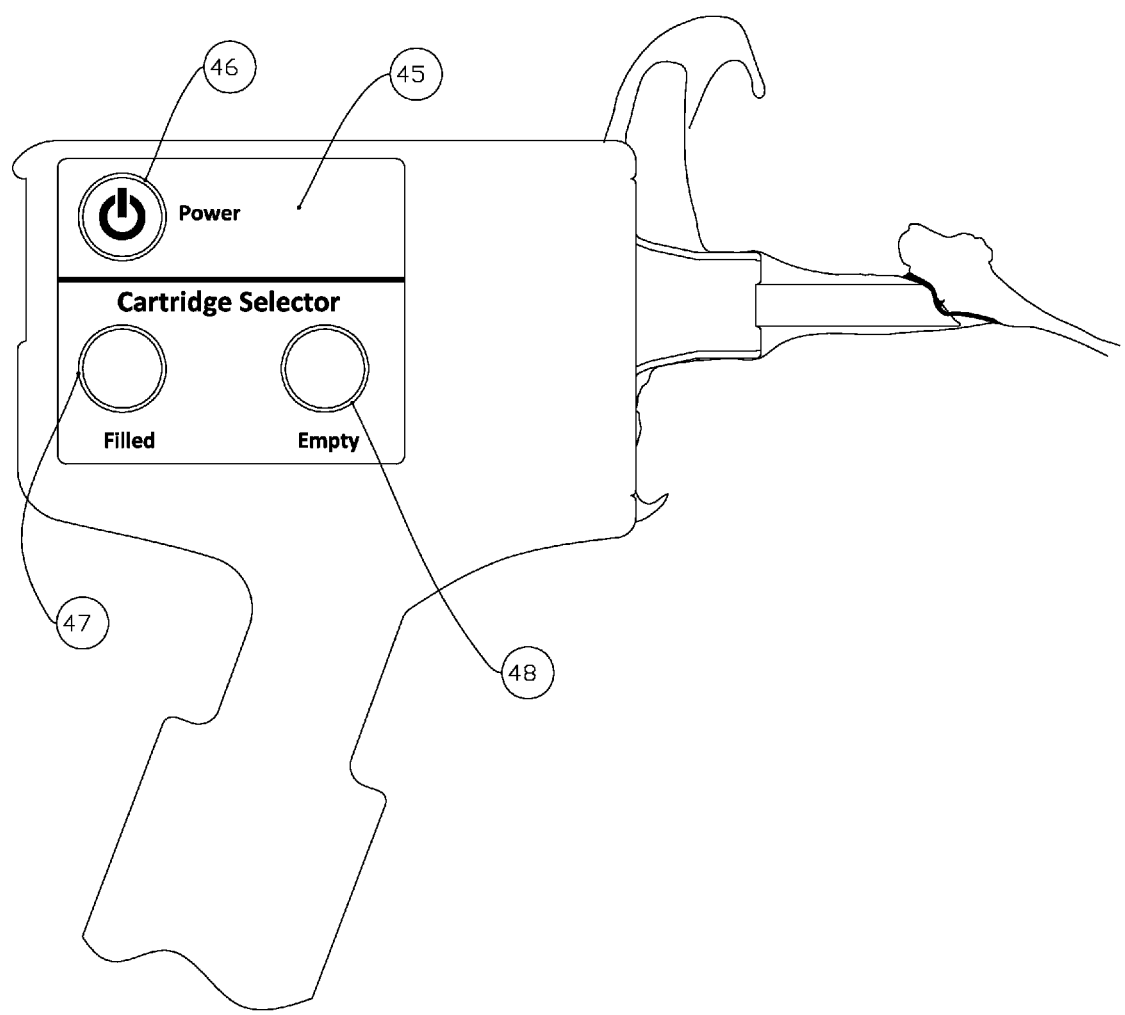
FIG. 6 shows the side view of the device in a fully-extended position, inserted into the ear canal.

In the preferred embodiment, the selector panel 45 is disposed on the side of the housing 5, as shown in FIG. 6. The device is turned on by depressing the power button 46. After the device is turned on, the user may select the type of movable body that has been inserted into the device. If the injection chamber 11a, shown in FIG. 4, is empty, the select button for empty cartridge 48 is depressed. The injection chamber 11a may also contain a substance, for example an antibiotic-steroid otic suspension such as Ciprodex®. If the injection chamber 11a contains a substance, the select button for filled-chamber cartridge 47 should be depressed.

Figure 5:
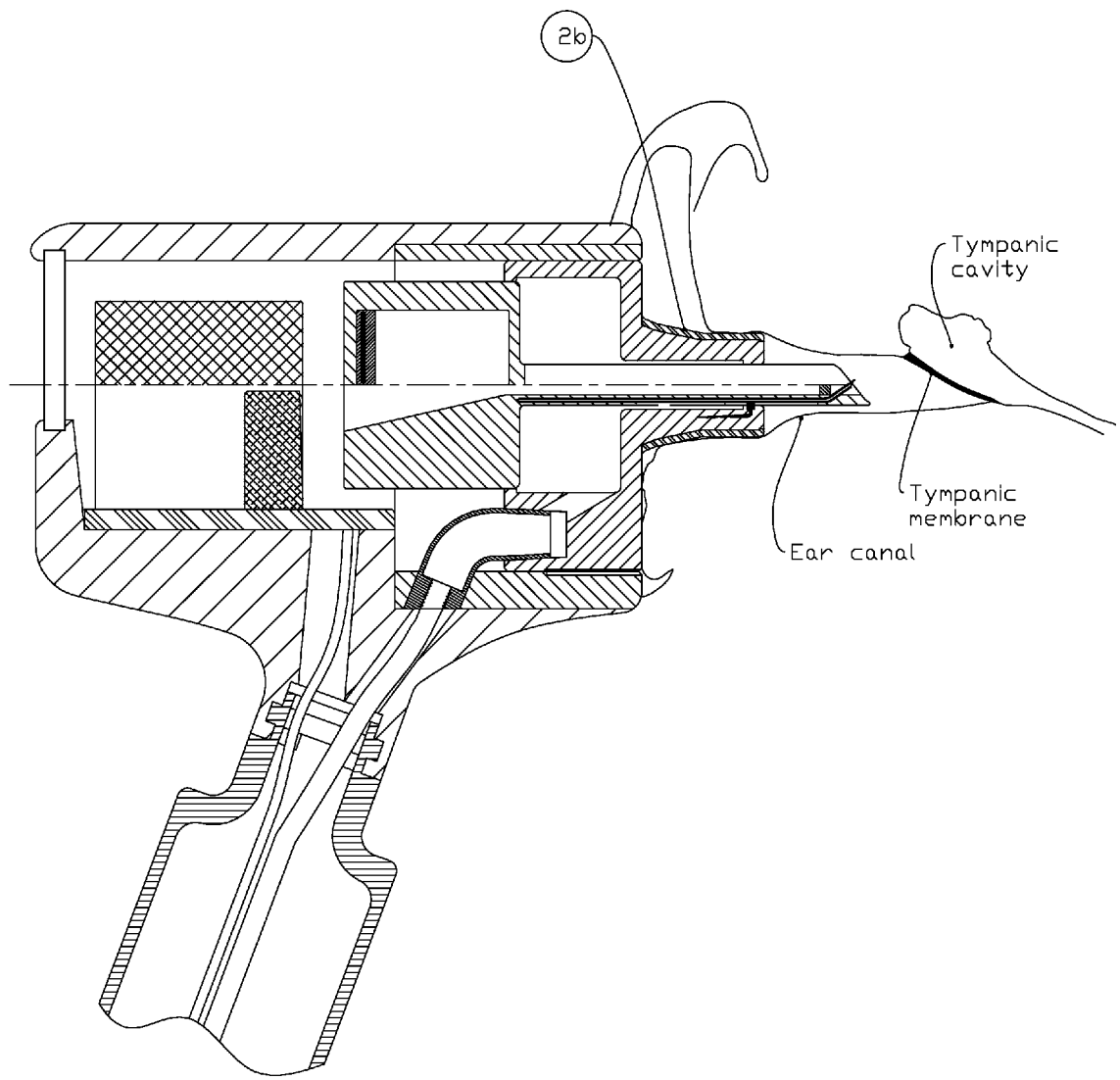
FIG. 5 shows the Section A-A of the device in a fully-retracted position, inserted into the ear canal.

The small section of the stationary body 2b is inserted into the ear canal of the patient and a slight vacuum seal is created between the ear canal tissue and small section of the stationary body 2b, as shown in FIG. 5. The small section of the stationary body 2b is approximately cylindrical. However, other suitable shapes, which would be obvious to those skilled in the art, can be used. In the preferred embodiment, the outer compressible layer of the stationary body 20 helps facilitate the vacuum seal between the stationary body 2 and the ear canal. When the small section of the stationary body 2b is inserted into the ear canal, the outer compressible layer 20 deforms and takes the shape of the ear canal, thereby creating an airtight seal. Underlying the outer compressible layer 20 is the inner rigid layer 20a. The outer compressible layer 20 can be made from any suitable material known to those skilled in the art. In the preferred embodiment, the outer compressible layer 20 is made from silicone, which is overmolded over the inner rigid layer 20a of the stationary body A compressible layer is not required to create a sufficiently airtight seal between the ear canal and the stationary body 2. After the small section of the stationary body 2b is inserted into the ear canal and the vacuum seal is created between the ear canal and the stationary body 2, a small amount of air is withdrawn from the ear canal to create the necessary vacuum. The air is withdrawn through the vacuum line 61, shown in FIG. 3, which is connected to the vacuum fitting 30. The vacuum fitting 30 is connected to the vacuum inlet 25 of the stationary body 2. After the vacuum valve 60 is opened, air flows out of the ear canal through the vacuum ports 26a, shown in FIGS. 2 and 4, and subsequently through the vacuum channels 26 in stationary body 2, thereby creating the necessary vacuum in the ear canal. Vacuum line 61 is connected to a commercially available vacuum pump. Various manual, mechanical, or electromechanical mechanisms for generating necessary vacuum may be used as standalone units that are connected to the device or may be incorporated into the device.

The back seal 22, shown in FIGS. 3 and 4, maintains the pressure difference between the distal surface of the movable body 1c and the proximal surface of the movable body 1d, by preventing air from entering into the ear canal. There are many ways to make a functionally-equivalent seal, which are known to those skilled in the art. For example, a rubber gasket or an o-ring can be used in either the movable body 1 or the stationary body 2 to create an airtight seal. Because the required vacuum is very low, in the preferred embodiment, the seal is not completely airtight; rather, the seal acts as a temporary barrier that impedes the air from entering through the back seal 22. Consequently, in the preferred embodiment the seal is created by having a sliding fit, with about 0.03 mm per side clearance between the movable body 1 and the back seal 22. The small clearance also allows the back seal 22 to function as a guide, approximately maintaining the motion of the movable body 1 in a predetermined path. Furthermore, because the back seal 22 allows some air to flow through, it serves as a safety mechanism, limiting the maximum vacuum in the ear cavity as well as the force on the movable body 1. The allowable clearance between the seal and the movable body depends on the size of the movable body 1, types of materials used for the stationary body 2 and the movable body 1, surface roughness, and the vacuum used to advance the movable body. In the preferred embodiment, the area of the cross-section of the large section of the movable body 2a is approximately 500 mm$^2$, and the vacuum used is about 40-70 Torr. The movable body 1 is made from medical grade polypropylene, and the stationary body 2 is made from Teflon® PFA Grade 445 HP (perfluoroalkoxy copolymer). There are many suitable materials that can be used for the movable body 1 and stationary body 2, which would be obvious to those skilled in the art. The vacuum range can be increased or decreased depending on the area of the cross-section of the largest portion of the movable body. However, higher levels of vacuum may be painful for the patient and, depending on the pressure in the tympanic cavity, may rupture the tympanic membrane. In the preferred embodiment, the force that is applied to the sliding body is less than 10N. Although greater force may be used, it might result in some additional discomfort to the patient.

Many mechanisms, known to those skilled in the art, can be used to advance the movable body toward the tympanic membrane such as electrical, mechanical, hydraulic, pneumatic, or their various combinations. For example, linear actuators, screw mechanisms, electromechanical and magnetic linear actuators, hydraulic or pneumatic actuators, as well as many other mechanisms known to those skilled in the art. The movable body 1 can also be moved manually inward and/or outward. The vacuum seal between the stationary body 2 and the ear canal may be unnecessary, depending on the method chosen for advancing the movable body 1 and whether vacuum is used in the ear canal to deflect the tympanic membrane toward the movable body 1.

The front guide 27, shown on FIG. 3, ensures that the movable body 1 moves approximately along a predetermined path. The front guide 27 does not have to function as a seal, although such functionality can be added without changing the operation of the device. Consequently, in the preferred embodiment, the clearance between the small section of the movable body 1b and the front guide 27 is about 0.08 mm per side. However, it would be obvious to those skilled in the art to choose a different suitable clearance.

In the preferred embodiment, the piercing elements 10a and 10b are made from 316 Stainless Steel. However, piercing elements can be made from a variety of suitable materials known to those skilled in the art, including nonmetallic materials. As shown in FIGS. 2 and 3, the piercing elements 10a and 10b glide over the piercing element contacts 23a and 23b respectively. The piercing element contacts 23a and 23b are disposed in the stationary body 2. Wires connect the piercing element contacts 23a and 23b to the stationary body contacts 24a and 24b respectively. When the stationary body 2 is inserted into the insert 3, the stationary body contacts 24a and 24b make connection with the insert contacts 32a and 32b respectively. Wires connect insert contacts 32a and 32b to the ohmmeter module 42, which is imbedded in the printed circuit board 4. The main power supply line 62 delivers the required power to the circuit board. The CPU 43 controls the sequence of operations. When the piercing elements contact the tympanic membrane, the measured resistance between the two piercing elements will change. This change will be detected by the ohmmeter module 42. At a predetermined time interval, such as less than a second after the change in resistance has been detected, electromagnetic clamps 31, shown in FIG. 4, are activated and move forward to clamp around the movable body 1. The electromagnetic clamps 31 prevent the movable body 1 from further motion in either inward or outward direction. The compression layer of electromagnetic clamp 31a is disposed on the parts of the electromagnetic clamps 31 that come into contact with the large section of the movable body 1a. The compression layer deforms around the movable body, to reduce deformation of the large section of the movable body 1a. The electromagnetic clamps provide the device with an additional safety measure and also aid in preventing movement of the movable body 1 if/when a substance is injected from and/or evacuated into the chambers 11a and/or 11b respectively. Other mechanisms known to those skilled in the art can also be used to both detect the final position of the movable body 1 and/or to fixate the movable body once it has reached the final position. For example, a pressure sensor can be used to detect contact of the movable body 1 with the tympanic membrane. Furthermore, in some embodiments, the injection/evacuation mechanism may be disposed within the movable body. Consequently, during the injection/evacuation operation, the movable body will not experience external forces from the injection/evacuation mechanism, and the electromagnetic clamps 31 would not be required to hold the movable body stationary during the injection/evacuation operation. After the procedure is completed, the speaker 44 can be used to signal the end of the process.

If the resistance between the piercing elements 10a and 10b changes again, after the piercing elements came into contact with the tympanic membrane, it is because the piercing elements came into contact with fluid in the tympanic cavity. Consequently, the device can also be used to detect the presence or absence of fluid in the tympanic cavity.

In the preferred embodiment, after the piercing elements 10a and 10b have penetrated the tympanic membrane, the substance (if any) located in the injection chamber 11a can be injected into the tympanic cavity, while the fluid located in the tympanic cavity (if any) can be evacuated. The injection chamber plunger 12a is disposed in the retracted position—at the proximal end of the chamber, away from the point of connection to the piercing element 10a; and the evacuation chamber plunger 12b is disposed in the fully-extended position—at the distal end of the chamber, closest to the connection point to the piercing element 10b. Further, the injection chamber is connected to the evacuation chamber with the vent channel 15. When the injection chamber plunger 12a moves forward, toward the distal end of the chamber, the air is drawn out of the evacuation chamber 11b. The reduction in air volume in the evacuation chamber 11b pulls the evacuation chamber plunger 12b backward, away from the distal end of the chamber. As the evacuation chamber plunger 12b moves backward, it creates a slight vacuum, which draws fluid from the tympanic cavity through the piercing element 10b and into the evacuation chamber 11b. Consequently, injection of a substance into and evacuation of the fluid from the tympanic cavity can be performed essentially simultaneously. There are other methods, known to those skilled in the art, which can be used to synchronize the injection and evacuation functions of the device. Furthermore, injection and evacuation need not be performed simultaneously and can be done sequentially. Also, only one of the functions, either injection or evacuation, can be performed independently, without performing the other function.

In the preferred embodiment, a magnetizable insert 13 is imbedded in the injection chamber plunger 12a, as shown in FIG. 3. The injection chamber plunger 12a is advanced forward via application of a magnetic field, which is created by the electromagnet 41, shown in FIG. 4. As discussed above, the movement of the injection chamber plunger 12a pulls back the evacuation chamber plunger 12b. If the injection chamber 11a does not contain any substance, and the device is used only for evacuation of fluid, the same function can be used, that is, an injection chamber plunger 12a can be pushed forward to pull back the evacuation chamber plunger 12b to evacuate the fluid from the tympanic cavity.

Many other mechanisms can be used to advance the injection chamber plunger 12a forward and/or move the evacuation chamber plunger 12b backward. For example, linear actuators, various screw mechanisms, electromechanical and magnetic linear actuators, hydraulic or pneumatic actuators, as well as many other mechanisms known to those skilled in the art can be used. Furthermore, the injection chamber plunger 12a and the evacuation chamber plunger 12b can be moved manually.

After injection and/or evacuation function is completed, the device can be removed from the patient's ear canal. In the preferred embodiment, the device sounds a long beep at the end of the injection/evacuation process. The end of the process is determined by the time elapsed from the commencement of the injection function. In the preferred embodiment, the time-delay between the commencement and the long beep, indicating the end of the process, is 10 seconds. There are many other ways, known to those skilled in the art, to determine whether the injection/evacuation has been completed. For example, a sensor can be used to determine the position of either the injection chamber plunger or evacuation chamber plunger. Also, there are many ways that the end of the procedure can be signaled to the user.

Figure 7:
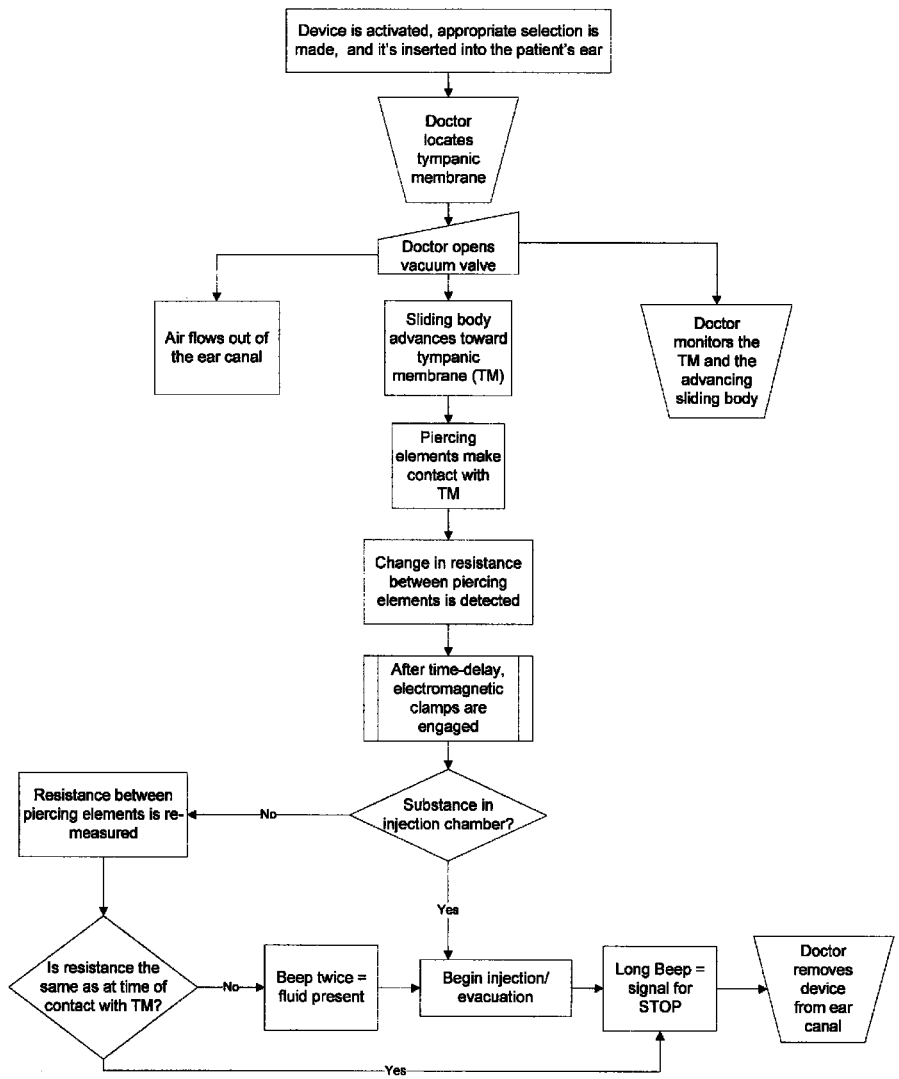
FIG. 7 shows a flowchart of the operations of the device.

FIG. 7 is an example of a sequence of operations of the device in the preferred embodiment. Not all of the operations in the sequence shown in FIG. 7 are essential to the invention. Likewise, a different sequence of the operations, which would not alter the essence of the invention, would be obvious to those skilled in the art. First, the device is activated (powered up), the user selects the type of cartridge that is inserted into the device, and the small section of the stationary body 2b is inserted into the patient's ear. Then, the user locates the tympanic membrane by looking through the viewing opening 18. Once the tympanic membrane is located, the user opens the vacuum valve 60. After the vacuum valve 60 is opened, the air flows out of the ear canal creating a slight vacuum. The slight vacuum creates a pressure difference between the distal surface of the movable body 1c and the proximal surface of the movable body 1d, which is exposed to the ambient pressure. This pressure difference applies a force that equals to the area of the cross-section of the large section of the movable body 1a×pressure difference; the force advances the movable body inward, toward the tympanic membrane. The user can maintain visual contact with the tympanic membrane while the movable body 1 advances inward. Subsequently, the movable body 1 makes contact with the tympanic membrane, and the piercing elements 10*a* and 10*b* penetrate the membrane. As the piercing elements make contact with the tympanic membrane, the ohmmeter module 42 detects the change in resistance between the piercing elements and after a time-delay of less than a second, electromagnetic clamps are activated and grip around the movable body 1. If the selection for an empty cartridge was made, the resistance between piercing elements is checked again. If the resistance is different than at the time of contact with the tympanic membrane, that indicates that there is fluid in the tympanic cavity, and the device beeps twice to notify the user of the presence of fluid. Subsequently, the injection/evacuation function is activated. If the resistance between the piercing elements did not change after the initial contact of the piercing elements with the tympanic membrane, this indicates that there is no fluid in the tympanic cavity, at least at the level reachable by the piercing elements. Subsequently, the injection/evacuation process will not be commenced, and a long beep will sound, signaling to the user that the procedure has been completed. If the user has preselected a cartridge that includes a substance for injection, the process of testing for presence of fluid can be bypassed, and injection/evacuation function is commenced after the electromagnetic clamps are engaged. Upon completion of the injection/evacuation function a long beep will sound, signaling the completion of the procedure.

What is claimed is:

1. A device for substance delivery to and/or extraction from the tympanic cavity of a patient, the device comprising:
    a stationary body having a small section that is sized and configured to be inserted into and seal an ear canal of the patient;
    a movable body disposed within the stationary body, the movable body being able to move relative to the stationary body and inward and outward relative to the ear canal;
    one or more piercing elements disposed within the movable body, the piercing element being configured to penetrate the patient's tympanic membrane; and
    a vacuum mechanism configured to reduce pressure in the ear canal, the reduction of pressure being sufficient to move the movable body inward relative to the ear canal.

2. The device as recited in claim 1, further comprising one or more vacuum ports sized and configured to allow the vacuum mechanism to withdraw air out of the ear canal, thereby reducing pressure in the ear canal.

3. The device as recited in claim 2, wherein the vacuum ports are located on the stationary body.

4. The device as recited in claim 1, wherein the one or more piercing elements are hollow piercing elements.

5. The device as recited in claim 4, further comprising one or more fluid-holding chambers, and wherein the one or more hollow piercing elements are in fluid connection with or serve as the one or more fluid-holding chambers.

6. The device as recited in claim 5, further comprising one or more of an injection mechanism and an evacuation mechanism.

7. The device as recited in claim 6, wherein the one or more of the injection mechanism and the evacuation mechanism are disposed within the movable body in a manner that the movable body does not experience external forces during an injection operation and during an evacuation operation.

8. The device as recited in claim 1, wherein the movable body comprises:
    a large section that defines a proximal portion of the movable body; and
    a small section that defines a distal portion of the movable body.

9. The device as recited in claim 1, further comprising a seal between the movable body and the stationary body.

10. The device as recited in claim 9, wherein the seal is not airtight.

11. The device as recited in claim 10, wherein the seal forms a sliding fit between the stationary body and the movable body.

12. The device as recited in claim 11, wherein the one or more piercing elements comprise a first piercing element and a second piercing element, and the device further comprises an ohmmeter module in electrical connection with the first and second piercing elements, the ohmmeter module being configured to measure change in electrical resistance between the first and second piercing elements.

13. A device for substance delivery to and/or extraction from the tympanic cavity of a patient, the device comprising:
    a stationary body having a small section that is sized and configured to be inserted into an ear canal of the patient;
    a movable body disposed within the stationary body, the movable body being able to move relative to the stationary body and inward and outward relative to the ear canal;
    a first piercing element and a second piercing element, the first and second piercing elements being configured to move inward relative to the ear canal, together with the movable body;
    an injection chamber in fluid connection with or formed by the first piercing element, the injection chamber having an injection plunger disposed therein; and
    an evacuation chamber in fluid connection with or formed by the second piercing element, the evacuation chamber having an evacuation plunger disposed therein, and the evacuation chamber being in fluid communication with the injection chamber in a manner that movement of the injection plunger produces movement of the evacuation plunger.

14. The device as recited in claim 13, further comprising a vent channel that provides fluid communication between the evacuation chamber and injection chamber.

15. The device as recited in claim 13, wherein movement of the injection plunger in a distal direction produces movement of the evacuation plunger in a proximal direction, the proximal direction being opposite to the distal direction.

16. A method of substance delivery to and/or extraction from a tympanic cavity of a patient, the method comprising:
    inserting a stationary body of a treatment device into an ear canal of the patient, wherein the treatment device includes a movable body sized and configured to move relative to the stationary body and into the ear canal;
    inducing movement of the movable body into the ear canal and toward a tympanic membrane of the patient by reducing air pressure within the ear canal; and
    penetrating the tympanic membrane with one or more piercing elements moving together with the movable body.

17. The method as recited in claim 16, further comprising one or more of injecting a substance into the tympanic cavity and evacuating a substance from the tympanic cavity through the one or more piercing elements.

18. The method as recited in claim 16, further comprising detecting contact with the tympanic membrane of a first piercing element and a second piercing element that comprise the one or more piercing elements.

19. The method as recited in claim 18, further comprising measuring resistance between the first and second piercing elements after detecting contact of the first and second piercing elements with the tympanic membrane.

20. The method as recited in claim 18, further comprising preventing the movable body from moving, a predetermined time interval after detecting contact of the first and the second piercing elements with the tympanic membrane.

* * * * *